(12) United States Patent
Butler et al.

(10) Patent No.: US 8,500,277 B1
(45) Date of Patent: Aug. 6, 2013

(54) OBJECTIVE TRAUMATIC BRAIN INJURY ASSESSMENT SYSTEM AND METHOD

(75) Inventors: Gene Butler, Albuquerque, NM (US); Gavin Erry, Malvern (GB); Paul Harrison, Rio Rancho, NM (US)

(73) Assignee: Kestrel Corporation, Albuquerque, NM (US)

( * ) Notice: Subject to any disclaimer, the term of this patent is extended or adjusted under 35 U.S.C. 154(b) by 121 days.

(21) Appl. No.: 13/196,746

(22) Filed: Aug. 2, 2011

Related U.S. Application Data

(60) Division of application No. 12/170,374, filed on Jul. 9, 2008, now Pat. No. 7,988,287, and a continuation-in-part of application No. 10/981,996, filed on Nov. 4, 2004, now Pat. No. 7,419,264.

(60) Provisional application No. 60/948,656, filed on Jul. 9, 2007.

(51) Int. Cl.
*A61B 3/10* (2006.01)

(52) U.S. Cl.
USPC .......................................................... 351/205

(58) Field of Classification Search
USPC .................. 351/200, 205, 206, 210, 211, 221
See application file for complete search history.

(56) References Cited

U.S. PATENT DOCUMENTS

| 6,595,642 | B2 | 7/2003 | Wirth | |
|---|---|---|---|---|
| 6,820,979 | B1 * | 11/2004 | Stark et al. | 351/206 |
| 7,988,287 | B1 | 8/2011 | Butler et al. | |

OTHER PUBLICATIONS

Alves, W M. et al., "Traumatic Brain Injury", Handbook of Neuroemergency Clinical Trials, 2006, 71-72.
Arbabi, Saman et al., "A Comparison of Prehospital and Hospital Data in Trauma Patients", The Journal of Trauma Injury, Infection, and Critical Care vol. 56, No. 5, 2004, 1029-1032.
Binder, Laurence M., "A Review of Mild Head Trauma. Part II: Clinical Implications", Journal of Clinical and Experimental Neuropsychology vol. 19, No. 3, 1997, 432-457.
Buechler, C. M. et al., "Variation Among Trauma Centers' Calculation of Glasgow Coma Scale Score: Results of a National Survey", The Journal of Trauma: Injury, Infection and Critical Care vol. 45, No. 3, 1998, 429-432.
Cowand, Jennifer L. et al., "Efficacy of Vestibular Rehabilitation", Otolaryngology—Head and Neck Surgery vol. 118, No. 1, 1998, 49-54.
Crossman, J. et al., "The Glasgow Coma Score—Reliable Evidence?", Injury vol. 29, No. 6, 1998, 435-437.
Gennarelli, Thomas A. et al., "Mortality of Patients with Head Injury and Extracranial Injury Treated in Trauma Centers", The Journal of Trauma vol. 29, No. 9, 1989, 1193-1202.
Gottshall, Kim et al., "Objective Vestibular Tests as Outcome Measures in Head Injury Patients", The Laryngoscope vol. 113, 2003, 1746-1750.
Gronwall, D. et al., "Cumulative Effect of Concussion", The Lancet vol. 22, No. 2, 1975, 995-997.
Harrison, P. et al., "In Vivo Measurement of Ocular Aberrations with a Distorted Grating Wavefront Sensor", In 6th International Workshop of Adaptive Optics for Industry and Medicine, Galway, Ireland, 2007, 1-6.
Kapoor, N. et al., "Vision Problems", Textbook of Traumatic Brain Injury, American Psychiatric Publishing, 2005, 1-4.

(Continued)

*Primary Examiner* — Joseph P Martinez
(74) *Attorney, Agent, or Firm* — Peacock Myers, P.C.; Janeen Vilven

(57) ABSTRACT

A system and method for determining the neurological function of a patient by examining ocular responses.

16 Claims, 10 Drawing Sheets

OTHER PUBLICATIONS

Levin, Harvey S. et al., "Neurobehavioral Outcome Following Minor Head Injury: A Three-Center Study", J. Neurosurg. vol. 66, 1987, 234-243.

Marion, Donald W. et al., "Problems with Initial Glasgow Coma Scale Assessment Caused by Prehospital Treatment of Patients with Head Injuries: Results of a National Survey", The Journal of Trauma vol. 36, No. 1, 1994, 89-95.

Marmarou, A., "Conduct of Head Injury Trials in the United States: The American Brain Injury Consortium (ABIC)", Acta Neurochir. vol. 66, 1996, 118-121.

Marshall, Lawrence F. et al., "Pitfalls and Advances from the International Tirilazad Trial in Moderate and Severe Head Injury", Journal of Neurotrauma vol. 12, No. 5, 1995, 929-932.

Maruenda, Francisco B., "Ref's Eye for the Fast Guy", StudentBMJ vol. 13, 2005, 8-9.

McNamee, Shane et al., "Vestibular Disturbances After Acute Mild Head Injury", Department of Physical Medicine and Rehabilitation, Richmond VAMC, 1-22.

Menegazzi, James J. et al., "Reliability of the Glasgow Coma Scale When Used by Emergency Physicians and Paramedics", The Journal of Trauma vol. 34, No. 1, 1993, 46-48.

Miller, Kelly J. et al., "Predictive Value of an Early Glasgow Outcome Scale Score: 15-Month Score Changes", J. Neurosurg. vol. 103, 2005, 239-245.

Nakase-Richardson, Risa et al., "Assessment of Traumatic Brain Injury", Handbook of Neurologic Rating Scales, 2006, 363-379.

Ngumah, Q. C., "Validity of Oculomotor Dysfunction as an Indicator of Traumatic Brain Injury", In Neurological Effects of Blast Injury, 2008, 1-3.

Rozema, Jos. J. et al., "Clinical Comparison of 6 Aberrometers. Part 1: Technical Specifications", J Cataract Refract Surg vol. 31, 2005, 1114-1127.

Selzer, Michael A. et al., "Rehabilitation Research & Development Service", VA'a Research & Development website http://www.research.va.gov/programs/pride/policy/default.cfm, 1-31.

Stanworth, A., "Defects of Ocular Movement and Fusion After Head Injury", Brit. J. Ophthal. vol. 58, 1974, 266-271.

Stocchetti, Nino et al., "Innacurate Early Assessment of Neurological Severity in Head Injury", Journal of Neurotrauma vol. 21, No. 9, 2004, 1131-1140.

Suchoff, I. B. et al., "Visual Impairment Related to Acquired Brain Injury", The Lighthouse Handbook on Vision Impairment, 2000, S19-S39.

U.S. Department of Health, "Guidance for Industry—E6 Good Clinical Practice: Consolidated Guidance", Food and Drug Administration Website http://www.fda.gov/cder/guidance/959fnl.pdf, 1996, 1-63.

Umile, Eric M. et al., "Dynamic Imaging in Mild Traumatic Brain Injury: Support for the Theory of Medical Temporal Vulnerability", Arch Phys Med Rehab vol. 83, 2002, 1506-1513.

Vanderploeg, Rodney D., "Traumatic Brain Injury within the VHA and DoD Systems of Health Care", VA Psychology Leadership Conference/APA, 2006, 1-39.

* cited by examiner

OBJECTIVE TRAUMATIC BRAIN INJURY ASSESSMENT SYSTEM AND METHOD

CROSS-REFERENCE TO RELATED APPLICATIONS

This application is a divisional of U.S. patent application Ser. No. 12/170,374, entitled "Objective Traumatic Brain Injury Assessment System and Method", filed on Jul. 9, 2008, and issued on Aug. 2, 2011 as U.S. Pat. No. 7,988,287, which claims priority to and the benefit of U.S. Provisional Patent Application Ser. No. 60/948,656, entitled "Objective Traumatic Brain Injury Assessment", filed on Jul. 9, 2007, and which is a continuation-in-part of U.S. patent application Ser. No. 10/981,996, entitled "Ophthalmic Aberrometer for Measuring Aberrations in the Eye" filed on Nov. 4, 2004, and issued on Sep. 2, 2008 as U.S. Pat. No. 7,419,264 and the specification and claims thereof are incorporated herein by reference.

STATEMENT REGARDING FEDERALLY SPONSORED RESEARCH OR DEVELOPMENT

Not Applicable.

BACKGROUND OF THE INVENTION

Traumatic brain injury (TBI) diagnosticians traditionally have relied on subjective evaluations of the degree of injury to the brain or wait for expensive, highly sophisticated instruments, like MRIs, to diagnose a patient for brain injury. In battlefield conditions access to MRIs on scene are not practical. Subjective evaluation leads to undiagnosed and untreated brain injury until the trauma has caused irreversible injury. Prompt objective diagnosis and rapid therapy to minimize the effects of the brain trauma are essential to reduce damaging side effects, reduce medical costs long term and to improve overall outcomes. The introduction of objective measurement tools will provide the clinician with the ability to quickly, reliably, and routinely determine and monitor the state of the patient's injury during the initial diagnosis and throughout the treatment and recovery process.

In addition to inflammatory, infectious or autoimmune insult of peripheral cranial nerve, nerve root or brain stem in addition to neoplastic involvement of peripheral cranial nerve, nerve root or brain stem is a significant healthcare problem worldwide. Crucial to proper treatment and prognosis is an accurate assessment of neurological function. Universally, TBI assessment is accomplished according to the Glasgow Coma Scale (GCS)[1]. However, this assessment is not entirely applicable to all situations and the ceiling effect associated with the GCS makes this neurologic rating scale less sensitive for monitoring milder cases of TBI[2]. This can lead to a delay in appropriate treatment during the critical 24 to 48 hours after a suspected TBI when secondary brain damage is most likely to occur. Examples of limitations with the GCS include intubated patients who cannot complete the verbal response category, patients with temporary paralysis, or patients who are unable to complete the motor response test, such as with those treated using the current practice of early sedation[3,4]. In addition, a patient's GCS rating can have significant variability from diagnostician to diagnostician owing to its largely subjective nature[5,6,7]. In a London study of emergency neurosurgical referrals, it was determined that only 51% of patients arrived with accurate GCS scores[8]. The inherent subjectivity of the GCS, coupled with the previously mentioned ceiling effect for mild TBI, can result in the premature discontinuation of treatment or discharge of patients still in need of monitoring or treatment. Ultimately a one-point variation in scoring can mean the difference in deciding to send a patient to a Level 1 trauma center or not, having a significant affect on the care the trauma patient receives. In response to some of these limitations, ways to improve classification of patients with TBI are being developed[9]. Improved TBI description will not only offer considerable value for clinical trials[10,11] but will also influence clinical management and specific therapies[12].

Based upon available evidence and medical understanding of the physiological factors involved, a method and system providing reproducible, objective measurements of visual system dysfunction can provide a reliable indication of Mild to Moderate levels of Traumatic Brain Injuries (MMTBI). Such data will prove useful not only in the initial diagnosis, but will have significant value for prognostic and rehabilitative purposes.

One aspect of the present invention provides a method to develop and demonstrate a field deployable instrument capable of obtaining reliable measurements of visual function that could be used in the early diagnosis of MMTBI patients.

Another aspect provides an apparatus to measure an ocular response that objectively measures visual function to detect MMTBI[31]. The system and method of the present invention provides one or more of the following advantages; ease of use, fast, non-invasive, and objective measurements from the initial classification of a patient's neurological state, through the early stage treatment, drug response/effect and into the rehabilitation process. The instrument's ease of use will allow for frequent monitoring of a patient's condition during longitudinal assessment thereby providing quick, reliable assessment for field and clinical environments alike.

A benefit of one embodiment of the system and method is application to the military personnel serving in today's overseas combat operation where the occurrence of MMTBI is a daily threat. The relationship between visual ocular response and specific neurological conditions has not previously been thoroughly investigated.

TBI occurs when a sudden trauma, such as a blow to the head or penetrating head injury disrupts the function of the brain. Although, numerous methods have been proposed to measure, and thus classify brain damage, the Glasgow Coma Scale (GCS) is most commonly used for initial assessment of severity of damage[1]. Patients with MMTBI may exhibit a range of visual system dysfunction, including binocular, oculomotor, accommodative, visual field loss, refractive error shift, and visual perceptual deficits[14,15]. Unfortunately, visual system assessment is often not performed during the acute stage of medical intervention; in fact, more often than not, incoming patients do not receive a thorough evaluation of their visual system at all. The reasons that visual assessments are not routinely performed include the lack of a standardized mechanism and protocol that will operate and be applicable under the largely varying situations present and the lack of an established, direct correlation with MMTBI. For example, TBI assessments are often made at different points in time and under greatly varying conditions, such as at the site of injury, during transportation to hospital, in the emergency room, or prior to admission.

Early detection of MMTBI is of particular importance to the Department of Defense. Average rates of brain injuries in deployed personnel are over twice as high as in the civilian population[16,17]. Inadequate diagnosis of MMTBI can have immediate consequence on operations and long-term impact on victims. Service members with no apparent symptoms after an assault or other physical injury can develop complications anywhere from 2 hours to 6 days after the initial injury[18]. Symptoms can include cognitive problems such as fatigue, irritability, anxiety, dizziness and visual disturbances, which can affect the ability to function, especially in a high-stress combat situation[19,20,21,22,23,24]. These individuals are at risk of being inadvertently returned to duty and presenting an adverse risk to themselves, their comrades and their missions.

The preferred diagnostic technique for head injuries in Combat Support Hospitals (CSH) is structural imaging using computerized tomography (CT). CT imaging provides more clinical information than can be obtained from physical examination of a patient. Unfortunately CT imaging may show as negative for mild to moderate trauma. Magnetic Resonance Imaging (MRI) is often the preferred diagnostic technique for other neurologic insults, or disease. With the addition of MRI, especially when integrated with single-photon emission computed tomography, measurements can more accurately show the physiological extent of a lesion, disease or other neurologic injury of the brain[25]. This outcome, which can be true even for MMTBI, assumes that a patient has been first, adequately identified as a potential MMTBI case, and second, enough time has passed that an identifiable lesion has formed. Even so, the physical size, operational complexity, and logistics of MRI preclude its use in every CSH. Thus, a new system and method for clinical and research use suitable for field use is required to bridge the gap between CT and MRI.

An objective technique for reliable and repeatable assessment of ocular response to access central and peripheral neurological function in potential MMTBI patients for example, would provide a complementary test of neurological function.

SUMMARY OF THE INVENTION

One embodiment of the present invention provides an ophthalmic examination device comprising a wavefront sensor aligned with an eye of a patient through a first optical path; a target aligned with the eye through a second optical path; a pupil imager aligned with the eye through the first optical path or the second optical path; wherein the wavefront sensor is positioned to measure the variation in the wavefront reflected from the retina of the eye via the first optical path. In a preferred embodiment a fundus imager is aligned with the eye through the first optical path or the second optical path. The target may be a physical target or a virtual target. A deformable mirror in the second optical path may produce changes in the position of the virtual target. Alternatively a mirror is mechanically altered to move the target to a new physical location. In another embodiment a deformable mirror in the first optical path, the second optical path or a combination thereof provides correction of refractive error. In yet another embodiment an illumination source is co-aligned to the first optical path, the second optical path or a combination thereof. In a more preferred embodiment, the device further comprises a binocular wherein both eyes share a common optical path to the target. In this embodiment, a mirror for correction of refractive error may be in the common path.

Another embodiment of the invention provides a method for determining neurological function of a patient comprising the steps of automatically measuring accommodation in both eyes of a patient simultaneously comprising presenting a target within an ophthalmic examination device to an eye of a patient to focus upon wherein the target is in a first position of the ophthalmologic examination device. A first wavefront of reflected light from the eye focused upon the target is measured using a wavefront sensor aligned with the eye via a first optical path. The target is moved to a second position while the eye is focused upon the target. A change in the wavefront measured from the eye when the target is moved to the second position is compared to the wavefront measured from the eye focused upon the target in the first position. A response time is determined of the eye to follow the target from the first position to the second position to determine the accommodation of the eye. In a preferred embodiment the response time for accommodation of the eye is compared to a database of control accommodation to produce an accommodation score.

Another embodiment of the present invention provides a method for determining neurological function comprising the steps of: automatically measuring saccades in both eyes of a patient simultaneously comprising: presenting a target within an ophthalmic examination device to an eye of a patient to focus upon wherein the target is in a first position of an ophthalmologic examination device. An eye tracking vector is calculated for each eye independently as each eye is focused upon the target. Motion of the vector is measured over time to determine saccades. In a preferred embodiment a movement above predetermined cutoff frequency is measured. In a more preferred embodiment a database of normal saccades to produce a saccades score.

Yet another embodiment of the present invention provides a method for determining neurological function comprising the steps of: automatically measuring vergence efficiency in both eyes of a patient simultaneously comprising: a) presenting a target within an ophthalmic examination device to an eye of a patient to focus upon; b) calculating an eye tracking vector for each eye independently as each eye is focused upon the target; c) determining the intersection of the left eye vector and right eye vector focused upon the target in a first position in comparison to the actual target position within the ophthalmic examination device; and d) determining the tracking accuracy of each eye by determining offset of an eye vector in comparison to calculated target position to determine vergence errors. In a preferred embodiment steps a)-d) are repeated as the target is moved to a second position; and vergence efficiency at a plurality of intermediate positions between the first and second target position is measured. In a more preferred embodiment, a movement below a predetermined cutoff frequency is measured. In yet another embodiment, the vergence errors determined are compared to a control database of vergence errors to produce a vergence efficiency score.

Yet another embodiment provides a method for determining neurological function comprising the steps of: automatically determining smooth pursuit in both eyes of a patient simultaneously comprising: presenting a target within an ophthalmic examination device to an eye of a patient to focus upon wherein the target is in a first position of an ophthalmic examination device; calculating an eye tracking vector for each eye independently as each eye is focused upon the target to produce a left eye vector and a right eye vector; determining the intersection of the left eye vector and right eye vector focused upon the target in comparison to the target position within the ophthalmic examination device; moving the target in a pattern; comparing each eyes temporal eye tracking of the moving target over time; and determining temporal correlation of each eyes movement to the moving target to determine smooth pursuit of each eye as an indication of neurological function. The pattern may be random or non-random. In a preferred embodiment a score as to the calculated smooth pursuit of each eye of patient is compared to a database of control values to produce a smooth pursuit score.

Yet another embodiment provides a method for determining neurological function comprising the steps of: automatically measuring pupillary response comprising: determining pupil size of each eye independently in a first light condition with a device as described in FIG. 1; comparing pupil sizes; measuring pupil response time of each eye after a change in light condition; and comparing the pupillary response time of each eye as an indication of neurological function. In a preferred embodiment a pupillary response is determined by providing a score as to the calculated pupillary response of each eye as compared to a control response.

Still another embodiment provides a method for determining neurological function of a patient comprising the steps of: generating a score reflective of the neurological function of a patient based upon one or more scores selected from eye accommodation score, eye vergence score, eye saccades score, eye smooth pursuit score, pupillary response score or any combination thereof to determine the neurological function of the patient.

In yet another embodiment, measurements of the eye are not taken simultaneously but are taken independent of the other eye.

It is an aspect of the present invention to evaluate neurological function with a system and method to monitor one or more of the following: accommodation, pupillary response, vergence, saccades, smooth pursuant using a field deployable instrument capable of obtaining reliable measurements of visual function that could be used in the early diagnosis of patients with brain injury, neurological disease or a combination thereof. For example, stroke, Multiple Sclerosis, Amylateral Sclerosis, polyneuropathy, mononeuritis multiplex, meningitis, head trauma.

On object of the present invention provides for a system and method for evaluating neurological function in patients having, stroke, Parkinson's, Post Traumatic Stress Disorder (PTSD), sports injuries and drug efficacy and toxicity.

Another aspect of the present invention provides an ophthalmic examination device to measure an ocular response that objectively measures neurological function to detect brain injury, neurological disease or a combination thereof. One embodiment of the present invention provides one or more of the following; ease of use, fast, non-invasive, consistent, and objective measurements from the initial classification of a patient's neurological state, through the early stage treatment through the rehabilitation process.

Another object of the present invention provides for ease of use of an ophthalmic examination device for frequent monitoring of a patient's condition during the entire treatment process, providing quick, reliable assessment for field and clinical environments alike.

Additional objects and advantages of the present invention will be apparent in the following detailed description read in conjunction with the accompanying drawing figures.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 1:
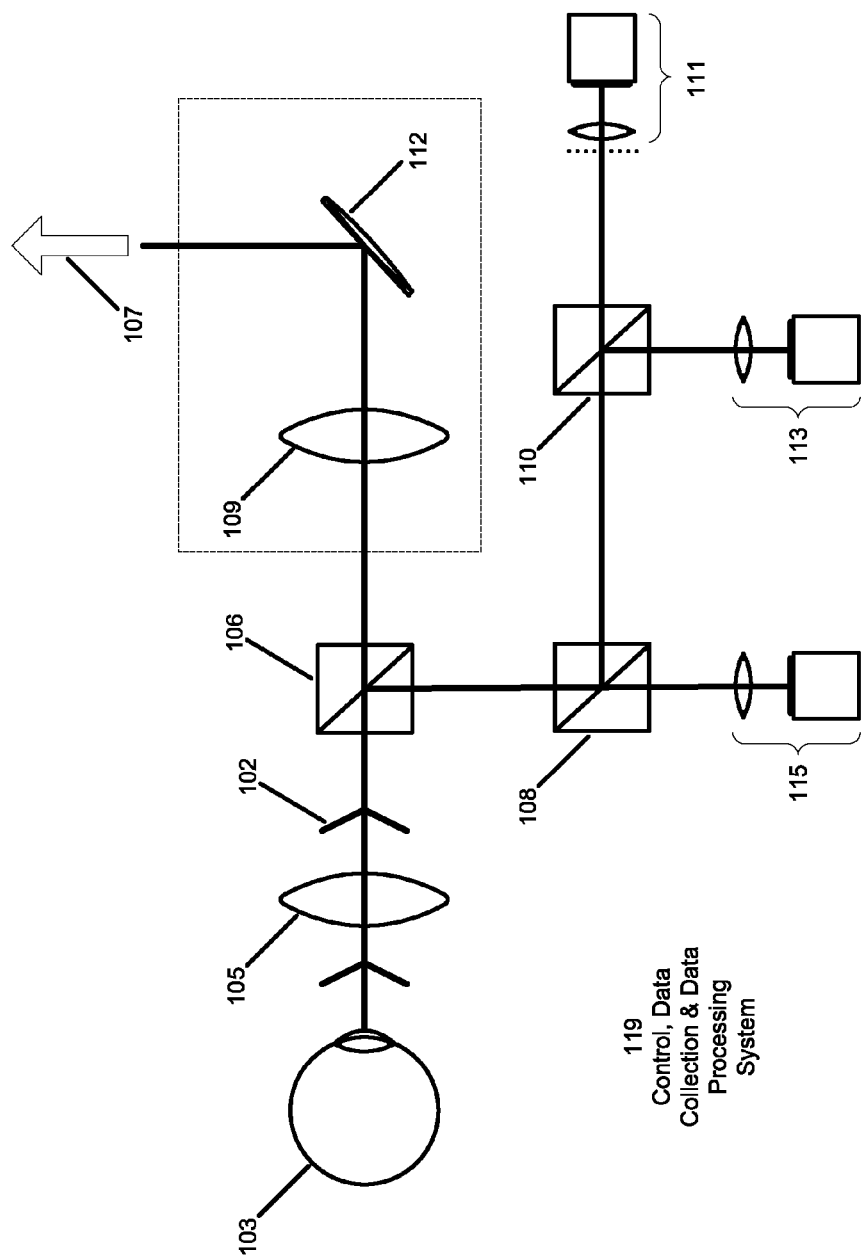
FIG. 1 illustrates one embodiment of the ophthalmic examination device.

Many aspects of visual functioning require communication among widely separated areas of the brain. The pathways connecting the retina to the primary visual cortex traverse its entire length. Injury to white matter connecting these widely spread vision-related areas may result in visual field deficits, changes in color vision, and/or oculomotor dysfunction. Oculomotor systems which govern eye movements and include vergences, accommodation, and versions, involve both brainstem, cortical and subcortical processing. Functional imaging studies have implicated multiple areas, including the paramedian pontine reticular formation, vermis of the cerebellum, superior colliculus, frontal and parietal eye fields, dorsolateral prefrontal cortex, visual cortex, vestibular cortex, basal ganglia and thalamus.

Injury to white matter connecting widely spread vision-related areas may result in visual field deficits, changes in color vision, and/or oculomotor dysfunction (e.g., vergence, accommodation, saccades, smooth pursuit), collectively termed the post-trauma vision syndrome.

A meta-analysis of three clinically measurable oculomotor associated functions from four (4) studies containing a combined population of control and TBI patients was performed. Oculomotor outcome variables (accommodation, vergence, and version) were measured. Pooled risk ratios for the incidence of accommodative abnormalities in subjects with TBI compared to subjects without TBI indicate an increased incidence in the subjects with TBI. Dispersion was uniform. Pooled risk ratios for the incidence of vergence abnormalities in subjects with TBI compared to subjects without TBI indicate an increased incidence in the subjects with TBI. Dispersion was uniform. Pooled risk ratios for the incidence of versional abnormalities in subjects with TBI compared to subjects without TBI indicate an increased incidence in the subjects with TBI. Dispersion was uniform.

The Mantel-Haenszel methods (the default fixed effect methods of meta-analysis programmed in RevMan) were used. Using this method, data from each study is weighted based on several parameters including the effect measure (relative risk (RR) in this case) and study size. The effect size represented as rate of an event in TBI/rate of an event in non-TBI control ranged from approximately 3×-7.7×.

The relative risks for dysfunctions of accommodation, vergences were described, thus allowing a metric as to the use of these oculomotor functions in the detection of TBI or as associated clinical predictors. For the meta-analysis the RevMan software was used in keeping with Cochrane Collaboration guidelines. All three measures of oculomotor function were significantly affected in TBI, with the greatest effect size occurring in vergence, followed by versions, and then accommodation. Heterogeneity in selected studies was estimated using I2=[(Q df)/Q]×100%, where Q is the chi-squared statistic and df is its degrees of freedom. The resulting percentage describes the variability in effect estimates that is due to heterogeneity rather than sampling error (chance). A value greater than 50% is usually considered substantial heterogeneity. All 12 values in this study were less than 50% signifying great levels of homogeneity among included studies. Based upon Applicant's observations a system and method for measuring neurological function of a patient with an embodiment of an ophthalmic examination device is described.

One embodiment of the present invention provides an ophthalmic examination device. Referring now to FIG. 1, one embodiment of the ophthalmic examination device is illustrated. An eye under examination 103 is aligned with a wavefront sensor 111 via a first optical path that passes through a beam splitter for example 106, 108 and 110. A target 107 is aligned with the eye via a second optical path for example a path that passes through 106. In a preferred embodiment, imager 113 is in the first optical path and images the pupil of the eye 103. In a preferred embodiment image 115 is in the first optical path and images the fundus of the eye 103. In a more preferred embodiment adaptive optics 105 correct for refractive error of the eye under examination. The correction can be manual or automatic. Image projection system 109 comprises optical components capable of varying apparent (image) longitudinal component of target 107 as well as a mirror capable of moving image laterally. Mirror 112 can be a deformable mirror or a mirror whose position is mechanically changed or a plurality thereof. The skilled practitioner in the art will readily recognize that based on mechanical convenience, wavelengths being used by different devices or other similar considerations there are a plurality of means to rearrange components and optical path branching points while still achieving the same functionality depicted in FIG. 1. All of these variations are within the scope and spirit of meaning for FIG. 1. For example, beam path 102 can be split by a beam splitter selectively for a defined wavelength. For example, beam splitter 106 may pass a portion of the light in the beam path from the target. For example, light having a wavelength of between about 400 nm to about 700 nm. For light reflected from the eye 103 to the beam splitter 106, the complimentary fraction of the light passed by the beam splitter 106 is directed by the beam splitter 106 to beam splitter 108 which may transmit/receive light having a wavelength of between about 400 nm to about 1000 nm. Imager 115 is tuned to wavelengths of about 550 nm, for example, while imager 113 and detector 111 may be tuned to about 750 nm to about 800 nm wavelengths. However, each beam splitter can be selected to transmit or receive a denied wavelength or range of wavelengths. Also the particular arrangement of imagers and sensor can be integrated in a first optical path or a second optical path without changing the function of the invention or its scope. Also, an imager or sensor can be integrated in a first optical path or a second optical path without changing the scope of the invention or its functions. An optical path is a path that a ray of light will follow through the system.

In a preferred embodiment both eyes are examined simultaneously with a binocular non-mydriatic ophthalmic examination device. In a more preferred embodiment, both eyes are examined simultaneously while observing a target in a common optical path. In a more preferred embodiment control data collection and data processing system 119 obtains information from one or more components 115, 113, 109, 107, 111 for measuring visual system efficiency such as defocus and spherical aberration measurement, high resolution eye tracking, virtual target projection to determine accommodation, vergences, saccades, smooth pursuit of eye and pupillary response from both eyes simultaneously, however, the device is not limited thereto as each eye can be observed independently in using a monocular device. However by simultaneously measuring both eyes for multiple parameters the patient is not fatigued with exposure to multiple instruments over time and improved measurements can be obtained.

An illumination source is co-aligned to a first optical path, a second optical path, or a combination thereof. An illumination source can be tuned to a wavelength that stimulates the eye or that is non-stimulating to the eye.

Real-Time Accommodation: Real time measurement of the aberrations in patients' eyes are observed, measured, determined, scored or some combination thereof with an ophthalmic examination device according to one embodiment of the present invention.

Figure 2:
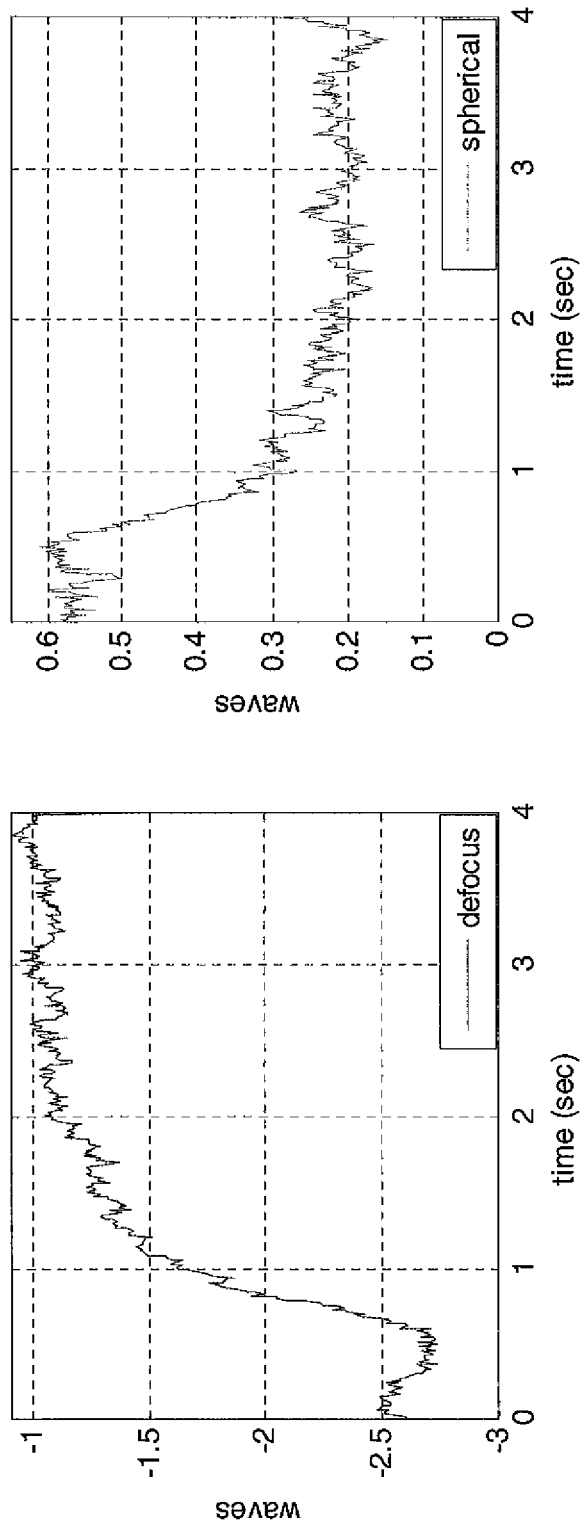
FIG. 2 is an example of accommodation for defocus (2a) and spherical (2b) observation from an eye with an ophthalmic examination device according to one embodiment of the present invention.

One embodiment of the present invention utilizes a wavefront sensor to generate defocus and spherical aberration measurement measurements. In a preferred embodiment, the wavefront sensor is a distorted grating wavefront sensor. The distorted grating wavefront sensor has several advantages, one of which is that the data to generate the aberration information is contained in a single, small-size image as compared to the amount of data required with a Shack-Hartman wavefront sensor. As very little data needs to be collected as compared to data collection with a Shack-Hartman wavefront sensor, the detector used can be rugged, inexpensive, and be operated at very high data acquisition rates for example a camera can be operated at high frame rates. Additionally, the processing algorithm used for the reconstruction of the aberration map is very insensitive to scatter sources that may be present in the eye[31]. Such advantages allow not only improved measurement of static accommodation in refractive accommodations, but also measurement of dynamic accommodation obtained as the subject refocuses between distances. Referring now to FIG. 2, an example of defocus and spherical aberration measurement is provided. FIG. 2(a) illustrates defocus measurement as detected from the wavefront sensor. FIG. 2(b) illustrates spherical aberration measurement as detected by the wavefront sensor. Together the measurements of defocus and spherical aberration of the eye provide an accommodation measurement based upon the time required for the aberration to reach steady state or some fraction thereof, for example, about 75% of steady state.

One of the common complaints associated with brain injury or disease is blurry vision. The blurry vision can be the result of neurological impairments, but it is also important to be able to conclusively rule out physiological (functional) causes for this impairment, such as refractive errors as a result of the injury, elevated pressures or pre-existing conditions in the patient. To rule out these problems, in a preferred embodiment, the system and method of the present invention are initially adjusts to provide refractive error correction. This correction can be done manually, much as is done by manual adjustments of binoculars. Alternatively, wavefront sensing and adaptive optics include an adaptive-optics based refractive correction upon system initialization. This system and method will ensure that vision defects and dysfunctions measured by the device are neurological.

Another embodiment provides for a dynamically varying target that can be seen by the patient. In one example, a liquid crystal display and projection optics allow the system to simulate targets that the patient will visualize at different distances and positions in the visual field. Varying the range of the target's apparent distance will stimulate the subjects' accommodation function enabling the aberrometer to obtain real-time measurements of accommodation.

Figure 3:
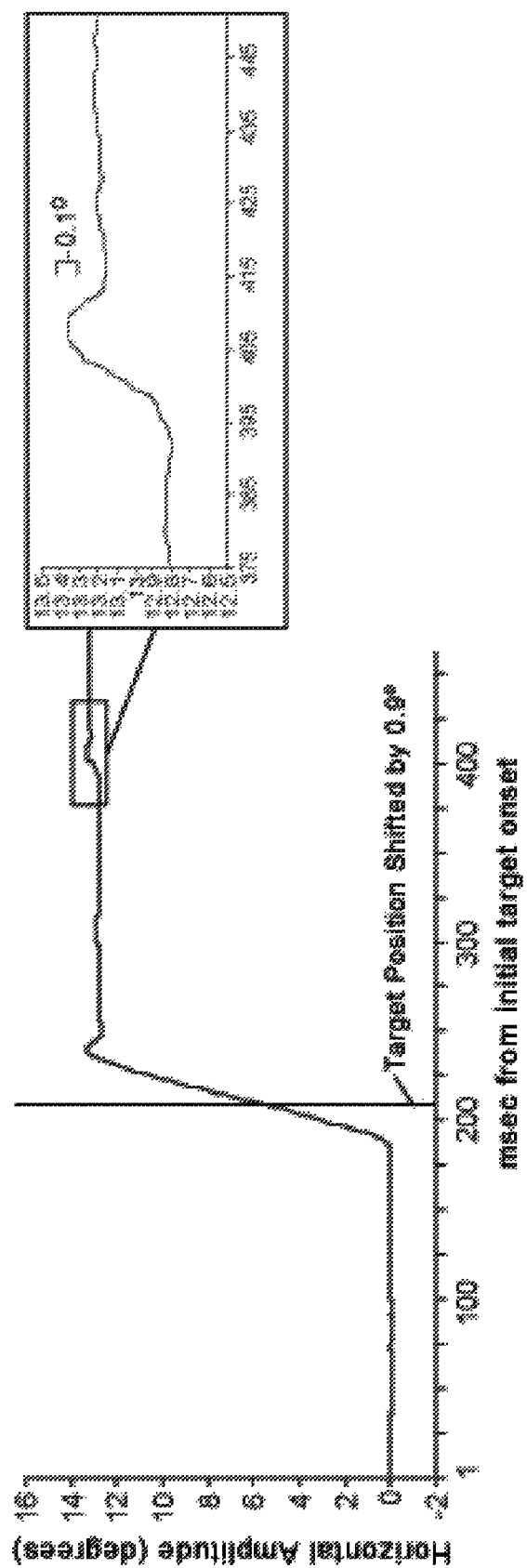
FIG. 3 illustrates an example of measurements of eye tracking with a prior art ophthalmic examination device.

Eye Tracking: Oculomotor function as an indicator of neurological function will be measured with improved resolution eye tracking having an improved degree of angular accuracy. Typically eye tracking systems are based on measurements made from a reference point within the pupil or on the cornea using either infrared or visible light. While these systems are ideal for general eye tracking applications, such as vision research[26], the accuracy of these systems is poor (0.5° typically). Such an error corresponds to an error distance of, approximately, 17 mm for a fixation distance of 2 m. This is clearly not accurate enough to observe the subtle defects in visual function such as double-vision that can occur from brain injury or disease such as MMTBI or other central and peripheral brain disease. For such measurements a very high degree of angular accuracy is required. For example, to achieve a measurement displacement of 1.7 mm at a 2 m fixation point, an angular accuracy of 0.05° is preferred, which is an order of magnitude smaller than that of currently available eye tracker systems. Referring now to FIG. 3, a typical eye tracking response is illustrated. The inset of the measurement illustrates sensitivity of low amplitude motion of the eye for normal resolution tracking observed with a prior art of ophthalmic examination device.

Figure 4:
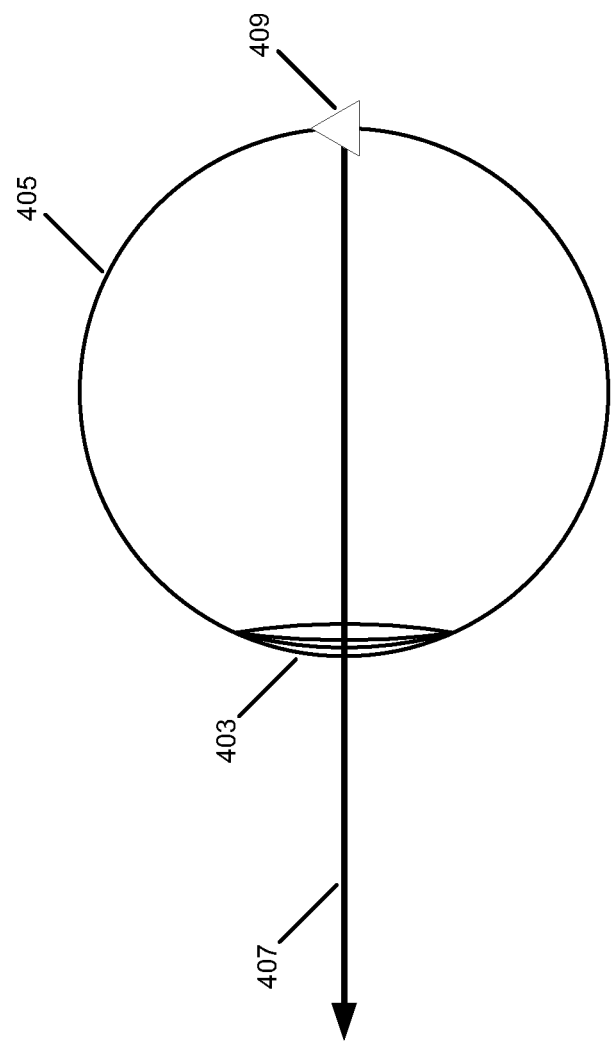
FIG. 4 illustrates a diagram of an eye tracking vector.

One embodiment of the present invention provides for a combined pupil and retina mapping technique. Referring now to FIG. 4, an eye tracking vector is determined for a patient's eye 409 according to one embodiment of the present invention. In a preferred embodiment a non-mydriatic binocular ophthalmic examination device acquires high speed images of the retina and pupil simultaneously from both eyes observing the same target. Using the pupil position 403 and retinal landmarks (such as the fovea) on the retina 405 a very accurate eye tracking vector 407 of eye direction can be calculated. As used herein the term eye tracking vector is defined as the line 407 from a position on the patient's optic disc 405 through a position about center of the patient's pupil 403 which defines a patient's central vision. As this is performed simultaneously in both eyes, the convergence of the two eyes can be determined. Using a displacement of 2 mm at a 2 m fixation point, the required displacement measurement on the retina is approximately 4 µm; making an accurate improved retina tracking system possible.

Figure 5:
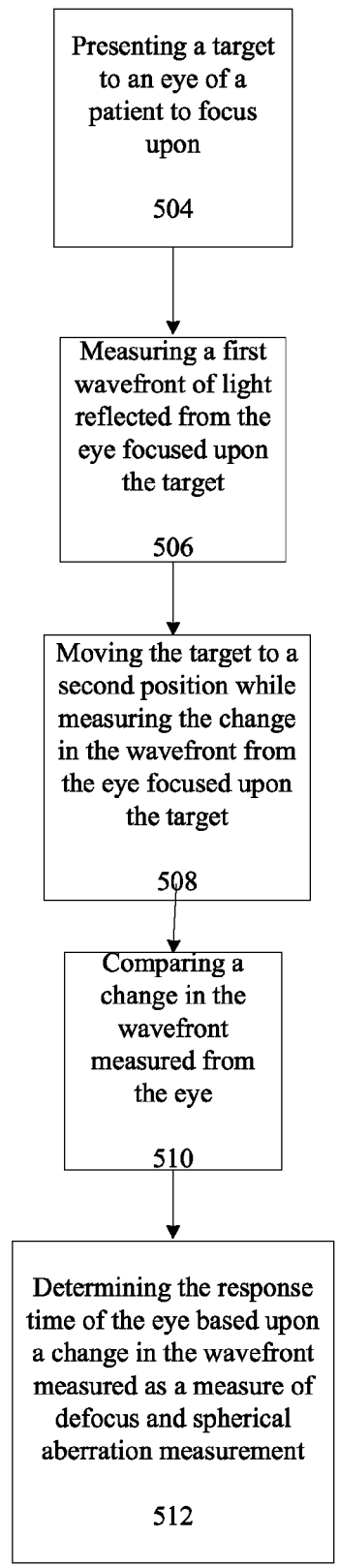
FIG. 5 illustrates a flow chart for the measurement of accommodation according to one embodiment of the present invention.

A target within the device allows the observer to measure the eyes accommodation as the target is in a static position and also when the target is repositioned. Referring now to FIG. 5, a flow chart of the steps to determine a patient's defocus and spherical aberration is illustrated according to one embodiment of the present invention. A target is presented to the patient's eye to focus upon 504. A wavefront reflected from the eye is measured from the eye focused upon the target 506. The target is moved to a second position while the change in the wavefront from the eye under examination is measured 508. The accommodation response time for the eye based upon a change in the wavefront measured indicates the eyes accommodation measurement. The accommodation measurement is an indication of the neurological health of the patient. The spherical and defocus measurement for a patient can be monitored longitudinally to determine the change over time of these eye measurements. Alternatively, the measurements may be compared to normal or control measurements. The normal or control database of measurements may be age similar controls or disease similar controls but not limited thereto.

In conjunction with information about the position of the target the accuracy of the visual direction of the two eyes relative to the target is calculated, and therefore a measure of the vergence characteristics is obtained. A vergence is the simultaneous movement of both eyes in opposite directions to obtain or maintain single binocular vision. The two eyes converge to point to the same object. When a creature with binocular vision looks at an object, the eyes must rotate around a vertical axis so that the projection of the image is in the centre of the retina in both eyes. To look at an object closer by, the eyes rotate towards each other convergence, while for an object farther away they rotate away from each other divergence. Exaggerated convergence is called cross eyed viewing (focusing on the nose for example). When looking into the distance, the eyes neither converge nor diverge. Vergence movements are closely connected to accommodation of the eye. Under normal conditions, changing the focus of the eyes to look at an object at a different distance will automatically cause vergence and accommodation.

Measurements of the instantaneous change of eye position can be monitored, as a target is switched from one position to another. The measurements will characterize the performance of the eyes individually and operating in concert, giving an accurate, objective assessment of any deficiency due to MMTBI or other central or peripheral disease or injury. The target can be a physical object or an image of a virtual target. In a preferred embodiment the target is a virtual target whose virtual position is changed with deformable mirrors.

Figure 6:
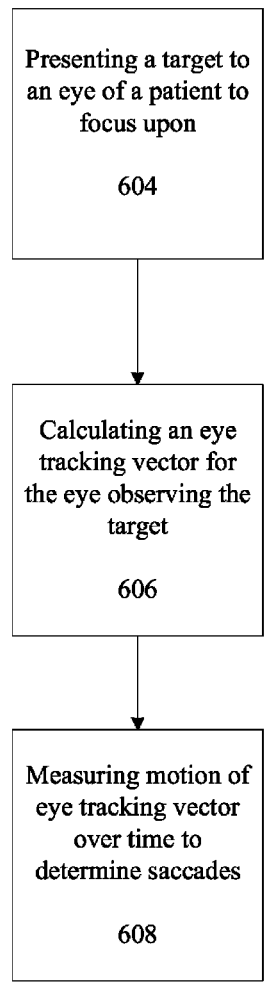
FIG. 6 illustrates a flow chart for the measurement of saccades according to one embodiment of the present invention.

Referring now to FIG. 6, one embodiment of the present invention provides for determining the saccades of the eye of a patient as an indication of the neurological function of the patient. A target is presented to a patient to focus upon 602. An eye tracking vector for each eye is calculated 604. The motion of the eye tracking vector over time is measured and the amplitude and frequency saccades over time are determined.

In another embodiment, the wavefront sensor and a deformable mirror system are the components needed to realize adaptive optics correction of refractive defects and make it possible to correct basic refractive errors as well as more complex problems such as oblique astigmatism that can render a patient unsuitable for fundus imaging. The adaptive optics correction also addresses issue of clarity of image being due to something other than neurological dysfunction.

Real Time Visual Stimulus: One embodiment of the present invention provides for measuring eye performance parameters. For example, a patient is asked to focus on a target that the subject can visualize. Traditionally these targets have been marks or small objects that are moved by the clinician. To measure the speed performance of the eye, a new type of target is required. The target changes position or range rapidly and at a precisely known point in the measurement sequence. One embodiment of the invention provides an automated target that is responsive to the measurement taken, the instructions of an algorithm operated on a computer and or the user.

It is known that the eye of a normal subject has a response-to-stimulus latency of approximately 360 ms, a fixation time from far-to-close of about 640 ms, and a time from close-to-far of 560 ms[27]. To measure these response times a target will be "moved" in time periods much smaller than this, on the order of tens of milliseconds. In a preferred embodiment the interval is less than 100 ms. In a more preferred embodiment the interval is between about 10-100 ms.

Figure 7:
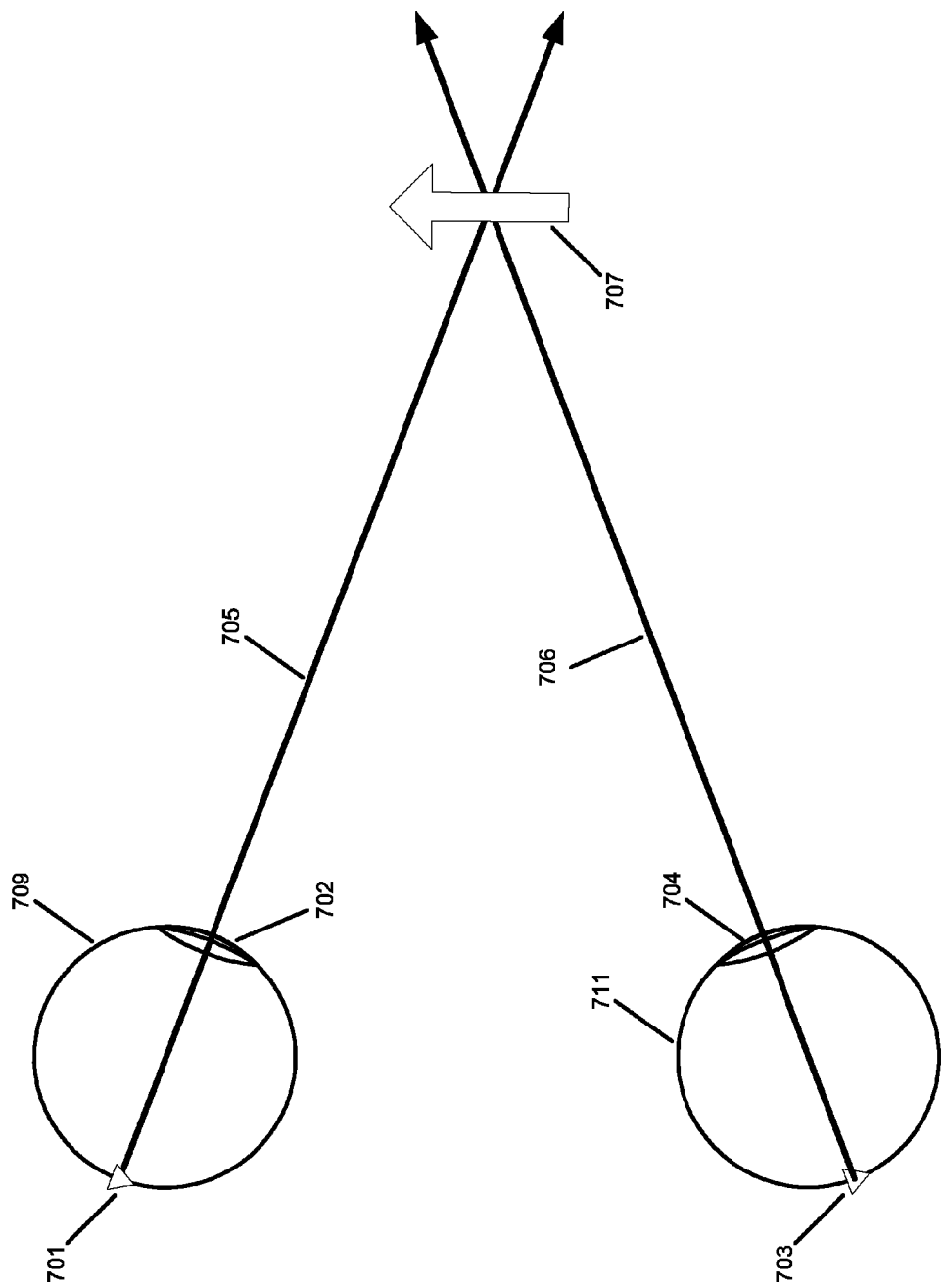
FIG. 7 illustrates vergence of both eyes focused on the same target.

Referring now to FIG. 7, the convergence point with the target is illustrated. From a retinal landmark 701 and a landmark on the pupil 702 on the left eye 709 a left eye tracking vector is determined which defines the line of vision 705 for the left eye when the eye is focused upon a target 707. Similarly, a retinal landmark 703 and a pupil landmark 704 on the right eye 711 is determined which defines the line of vision 706 for the right eye when the eye is focused upon a target 707.

For example, vergence measurements are acquired from both eyes while observing the same object which will require the two eyes to observe the object through the same optical path within an ophthalmic examination device. A preferred embodiment of the ophthalmic device includes a non-mydriatic binocular. This will ensure that both eyes of a patient are properly converging to the same point in object space. A common path configuration will avoid the possibility of convergence errors due to misalignment in the equipment, which would be possible when using a separate target for each eye. It is also possible to envisage a setup where there are two targets that are adjusted independently with each eye observing a separate target.

Figure 8:
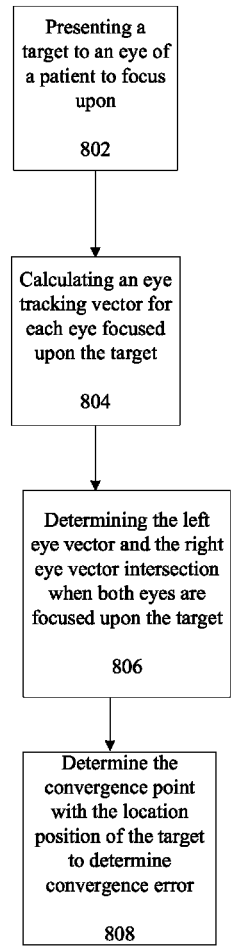
FIG. 8 illustrates a flow chart for the measurement of vergence according to one embodiment of the present invention.

Referring now to FIG. 8, the vergence error of a patient's eyes is determined as an indication of the neurological health of the patient. A target is presented to an eye of the patient 802. An eye tracking vector for each eye is determined when the eye is focused upon the target 804. The left eye vector and the right eye vector intersect when both eyes are focused upon the target is determined 806. The convergence error is determined by comparing the location of the target with the intersection point 808.

According to one embodiment of the present invention, a virtual target system has a response times far shorter than the accommodation time of the eye as discussed above. This allows measurement of the time taken for the eye to adjust to the target position. Due to the short time scale as discussed above, traditional adjustable optics based on mechanical movement of lenses is not preferred, so the use of deformable mirrors is preferred. Traditionally, deformable mirrors have been developed to combat the effects of atmospheric turbulence on the imaging performance of large telescopes. Based on the small mechanical actuation of a semi-flexible mirror it is possible to very accurately control the light reflecting off the surface. By controlling just the defocus term, these mirrors make an ideal candidate for an optical system that is instantly reconfigurable. Using several mirrors in conjunction will create a virtual target that can move to a protocol-defined distance from the observer. Particularly for measurement systems used for the eye, adapting to the individual peculiarities of each eye is frequently an essential precondition for eliminating or limiting sources of error or even the precondition for results capable of evaluation.

Figure 9:
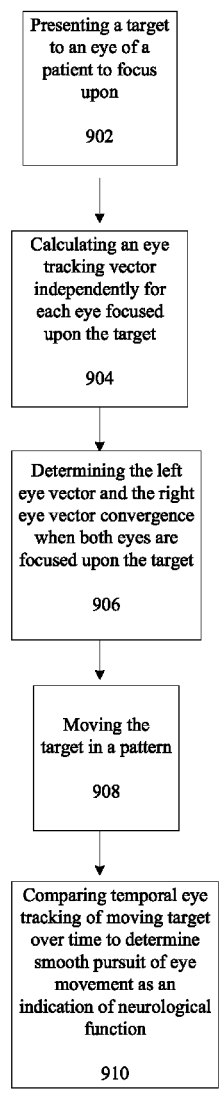
FIG. 9 illustrates a flow chart for the measurement of smooth eye pursuit according to one embodiment of the present invention.

Referring now to FIG. 9, a flow chart of the determination of smooth pursuit of the eye to a moving target is determined as an indication of the neurological health of the patient. A target is presented to both eyes of a patient to focus upon 902. An eye tracking vector is independently determined for each eye focused upon the target 904 which identifies a line of vision for each eye. The intersection of the line of vision for both eyes is determined and compared to the position of the target 906. The target is moved in a pattern and the each eye's ability to follow the moving target is detected 908. The temporal eye tracking of the moving target as compared to the position of the target over time is measured to indicate the smooth pursuit of the eye as an indication of the neurological health of the patient 910.

Figure 10:
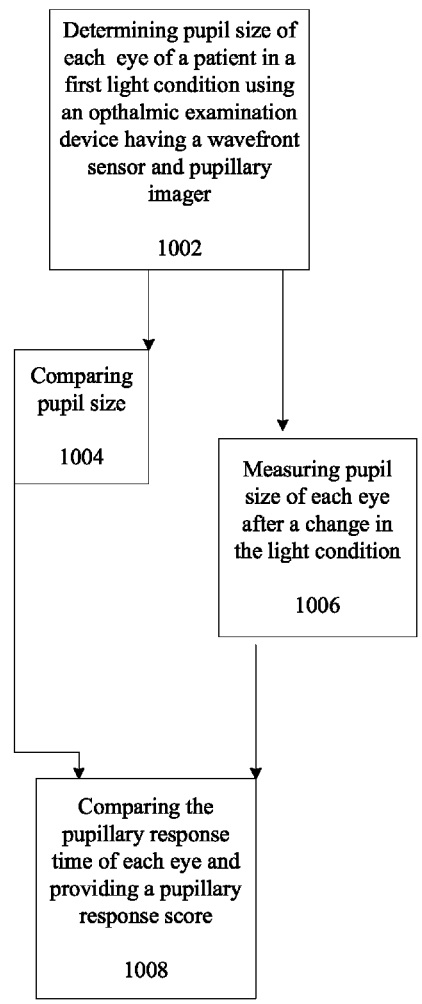
FIG. 10 illustrates a flow chart for the measurement of pupillary response according to one embodiment of the present invention.

Another common observed ocular defect is asymmetric pupils after concussion. One embodiment of the present invention images the pupil to determine location and centroid. Simultaneously, the image processing system can return the sizes of both pupils in response to the same stimuli, rather than performing independent pupillometry measurements in those situations where the additional information can enhance the understanding of the patient's condition by detecting assumptive or delayed stimulus responses. Referring now to FIG. 10, a flow diagram of the determination of the pupillary response as an indication of the neurological function of the patient is illustrated according to one embodiment of the present invention. The pupil size of each eye is determined under a first light condition 1002. The size of each pupil each compared to the other 1004. The size of each pupil is determined in a second light condition 1006. Comparing the pupillary response time of each eye for each condition 1008. Providing a pupillary response score.

The entire disclosures of all references, applications, patents, and publications cited above and/or in the references, and of the corresponding application(s), are hereby incorporated by reference.

REFERENCES

1. Jennett B J, Teasdale G. Management of Head Injuries. Philadelphia, Davis, 1981.
2. Nakase-Richardson R, Spinosa F, Swearingen C F, Eposito D. Assessment of traumatic brain injury. In: Herndon R M, editor. Handbook of neurologic rating scales. New York: Demos Medical Publishing, Inc.; 2006.
3. Marion D W and Carlier P M. Problems with initial Glasgow Coma Scale assessment caused by prehospital treatment of patients with head injuries: results of a national survey. J. Trauma. 36: 89-95, 1994.
4. Stocchetti N, et al. Inaccurate early assessment of neurological severity in head injury. Neurotrauma. 21:1131-40, 2004.
5. Menegazzi J J, Davis E A, Sucov A N, Paris P M. Reliability of the Glasgow Coma Scale when used by emergency physicians and paramedics. J. Trauma. 34: 46-8, 1993.
6. Buechler C M, et al. Variation among trauma centers' calculation of Glasgow Coma Scale score: results of a national survey. J. Trauma. 45: 429-32, 1998.
7. Arbabi S, et al. A comparison of prehospital and hospital data in trauma patients. J. Trauma. 56:1029-32, 2004
8. Crossman J, Bankes M, Bhan A, Crockard H A. The Glasgow Coma Score: reliable evidence of Injury. 29:435-7, 1998
9. Gennarelli T A, et al. Mortality of patients with head injury and extracranial injury treated in trauma centers. J. Trauma. 29: 1193-1202, 1989
10. Marshall L F and Marshall S B. Pitfalls and advances from the international tirilazad trial in moderate and severe head injury. J. Neurotrauma. 12: 929-932, 1995
11. Marmarou A. Conduct of head inury trials in the United States: the American Brain Injury Consortium (ABIC). Acta Neurochir. 66(suppl): 118-121, 1996
12. Alves W M and Marshall L F. Traumatic brain injury. In Alves W M, Skolnick B E, editors. Handbook of neuro-emergency clinical trials. Burlington, Elsevier, 2006
13. Miller K J, Schwab K A Warden N, et al Predictive value of an early Glasgow Outcome Scale score: 15-month score changes. J Neurosurg 103:239-245, 2005

14. Kapoor N, Ciuffreda K J. Vision problems. In: Silver J M, McAllister T W, Yudofsky S C, editors. Textbook of traumatic brain injury. Arlington (Va.): American Psychiatric Publishing; 2005
15. Suchoff I B, Gianutsus R, Ciuffreda K, et al. Visual impairment related to acquired brain injury. In: Silverstone B, Lang M A, Rosenthal B, et al. The Lighthouse handbook on vision impairment. New York: Oxford University Press; 2000.
16. Vanderploeg R D. Traumatic Brain Injury within the VHA and DoD Systems of Health Care.
17. Tampa VAMC, VA Psychology Leadership Conference/APA; April 2006.
18. Gottshall K, Drake A, Gray N, McDonald E, Hoffer M E. Objective vestibular tests as outcome measures in head injury patients. Laryngoscope. 11:1746-50, 2003.
19. Binder L M. A review of mild head trauma. Part II: Clinical implications. J Clin Exp Neuropsychol. 19:432-57, 1997.
20. Levin H S, Mattis S, Ruff R M, Eisenberg H M, Marshall L F, Tabaddor K, High W M Jr, Frankowski R F. Neurobehavioral outcome following minor head injury: a three-center study. J. Neurosurg. 66:234-43, 1987.
21. Gronwall D, Wrightson P. Cumulative effect of concussion. Lancet. 22; 2:995-7,1975.
22. Whitney S L, Rossi M M. Efficacy of vestibular rehabilitation. Otolaryngol Clin North Am. 33:659-72, 2000.
23. Kirtane M V, Medikeri S B, Karnik P P. E.N.G. after head injury. J Laryngol Otol. 96:521-8, 1982.
24. Tuohimaa P. Vestibular disturbances after acute mild head injury. Acta Otolaryngol Suppl. 359:3-67, 1978.
25. Umile E M, Sandel M E, Alavi A. Dynamic imaging in mild traumatic brain injury: support for the involvement of medial temporal vunerability. Arch Phys Med Rehabil. 83:1506-1513, 2002.
26. Applied Science Laboratories. www.a-s-l.com
27. Belda Maruenda F. Ref's eye for the fast guy. StudentBMJ, 13:8-9, January 2005.
28. VA's Research & Development website, Policy & Guidance: http://www.research.va.gov/programs/pride/policy/default.cfm
29. DeMarinis A J, Saunders C, Swarz H, Standard Operating Procedures for Good Clinical Practice by Sponsors, 2001; 2004 ISBN: 1-931107-57-2
30. Food and Drug Administration website, Guidance Documents: http://www.fda.gov/cder/guidance/959fnl.pdf
31. Ngumah, Q. C., et al. Validity of oculomotor dysfunction as an indicator or Traumatic Brain Injury. In Neurological Effects of Blast Injury. 2008.
32. Harrison P, Diaz-Santana L, Cuevas D, Erry G R G, Fournier P, Torti C. In Vivo Measurement of Ocular Aberrations with a Distorted Grating Wavefront Sensor. In 6th International Workshop on Adaptive Optics for Industry and Medicine, Galway, Ireland, 2007.
33. Rozema J J, MSc, Van Dyck D E M, Tassignon M J. Clinical comparison of 6 aberrometers. Part 1: Technical specification. J Cataract Refract Surg 31, 1114-1127. 2005.

What is claimed is:

1. A method for determining neurological function of a patient comprising the steps of:
  automatically measuring accommodation in both eyes of a patient simultaneously comprising:
    presenting a target within an ophthalmic examination device to an eye of a patient to focus upon wherein the target is in a first position of the ophthalmologic examination device;
    measuring a first wavefront of reflected light from the eye focused upon the target using a wavefront sensor aligned with the eye via a first optical path;
    moving the target to a second position while the eye is focused upon the target;
    comparing a change in the wavefront measured from the eye when the target is moved to the second position from the first position; and
    determining a response time of the eye to follow the target from the first position to the second position to determine the accommodation of the eye.

2. The method of claim 1 further comprising the step of comparing the response time for accommodation of the eye to a database of control accommodation to produce an accommodation score.

3. The method of claim 1 wherein the target is a virtual target.

4. The method of claim 3 wherein the virtual position of the virtual target is changed with a deformable mirror.

5. A method for determining neurological function comprising the steps of:
  automatically measuring pupillary response comprising:
    determining pupil size of each eye independently in a first light condition with a device as described in claim 1;
    comparing pupil sizes;
    measuring pupil response time of each eye after a change in light condition; and
    comparing the pupillary response time of each eye as an indication of neurological function.

6. The method of claim 5 further comprising providing a score as to the calculated pupillary response of each eye as compared to a control response.

7. A method for determining neurological function comprising the steps of:
  automatically measuring saccades in both eyes of a patient simultaneously comprising:
    presenting a target within an ophthalmic examination device to an eye of a patient to focus upon wherein the target is in a first position of an ophthalmologic examination device;
    calculating an eye tracking vector for each eye independently as each eye is focused upon the target;
    measuring motion of the vector over time to determine saccades.

8. The method of claim 7 wherein a movement above predetermined cutoff frequency is measured.

9. The method of claim 7 further comprising comparing the saccades determined to a database of normal saccades to produce a saccades score.

10. A method for determining neurological function comprising the steps of:
  automatically measuring vergence efficiency in both eyes of a patient simultaneously comprising:
    a) presenting a target within an ophthalmic examination device to an eye of a patient to focus upon;
    b) calculating an eye tracking vector for each eye independently as each eye is focused upon the target;
    c) determining the intersection of the left eye vector and right eye vector focused upon the target in a first position in comparison to the actual target position within the ophthalmic examination device; and
    d) determining the tracking accuracy of each eye by determining offset of an eye vector in comparison to calculated target position to determine vergence errors.

11. The method of claim 10 further comprising
repeating steps a)-d) as the target is moved to a second position;
measuring vergence efficiency at a plurality of intermediate positions between the first and second target position.

12. The method of claim 11 further comprising comparing the vergence errors determined to a control database of vergence errors to produce a vergence efficiency score.

13. The method of claim 10 wherein a movement below a predetermined cutoff frequency is measured.

14. A method for determining neurological function comprising the steps of:
automatically determining smooth pursuit in both eyes of a patient simultaneously comprising:
presenting a target within an ophthalmic examination device to an eye of a patient to focus upon wherein the target is in a first position of an ophthalmic examination device;
calculating an eye tracking vector for each eye independently as each eye is focused upon the target to produce a left eye vector and a right eye vector;
determining the intersection of the left eye vector and right eye vector focused upon the target in comparison to the target position within the ophthalmic examination device;
moving the target in a pattern;
comparing each eyes temporal eye tracking of the moving target over time; and
determining temporal correlation of each eyes movement to the moving target to determine smooth pursuit of each eye as an indication of neurological function.

15. The method of claim 14 wherein the pattern is random or non-random.

16. The method of claim 15 further comprising providing a score as to the calculated smooth pursuit of each eye of patient as compared to a database of control values.

* * * * *